(12) United States Patent
Gondhalekar et al.

(10) Patent No.: US 7,799,546 B2
(45) Date of Patent: Sep. 21, 2010

(54) THREE-STEP BIOMETHANATION PROCESS

(75) Inventors: Santhosh Gondhalekar, Pune (IN); Arvind Joshi, Pune (IN); Shreekant Patwardhan, Pune (IN); Neelesh Kulkarni, Pune (IN); Vijay Paranjpye, Pune (IN)

(73) Assignee: Gangotree Resource Developers (IN)

( * ) Notice: Subject to any disclaimer, the term of this patent is extended or adjusted under 35 U.S.C. 154(b) by 374 days.

(21) Appl. No.: 12/065,764

(22) PCT Filed: Aug. 30, 2006

(86) PCT No.: PCT/IN2006/000330
§ 371 (c)(1), (2), (4) Date: Mar. 5, 2008

(87) PCT Pub. No.: WO2007/052306
PCT Pub. Date: May 10, 2007

(65) Prior Publication Data
US 2008/0187976 A1 Aug. 7, 2008

(30) Foreign Application Priority Data
Sep. 5, 2005 (IN) .................. 1063/MUM/2005

(51) Int. Cl.
C12P 5/02 (2006.01)
(52) U.S. Cl. .................................... 435/167
(58) Field of Classification Search ................ None
See application file for complete search history.

(56) References Cited

U.S. PATENT DOCUMENTS

| 5,630,942 A | 5/1997 | Steiner | |
|---|---|---|---|
| 2004/0035785 A1* | 2/2004 | Rebholz | 210/603 |

OTHER PUBLICATIONS

Gondhalekar et al., A Triphasic Biomethanation Process, Oct. 14, 2005, The Patent Office Journal(India), p. 23038.
International Search Report for PCT/IN2006/000330, pp. 1-3, Pub date May 10, 2007.

* cited by examiner

Primary Examiner—Herbert J. Lilling
(74) Attorney, Agent, or Firm—Brooks Kushman P.C.

(57) ABSTRACT

A triphasic biomethanation process, to convert starch or sugary agricultural feed stock into a methane rich gas mixture for facilitating generation of biogas to be used as kitchen fuels, electrical power or transportation from renewable biomass in a cost-effective manner. The process brings about conversion of starch-rich or sugar-rich biomass into methane through three stages, namely, hydrolysis, acidogenesis and methane formation. The present invention deploys enzymes/physical/microbial parameters to hasten the hydrolytic reaction in the first stage. It also deploys microbial consortia that have been enriched for a targeted feed in order to speed up the process of conversion. The formation of alcohol from starch is prevented, as a result of the consortia deployed, the conversion efficiency is substantially improved and the retention time is also reduced to cut the capital cost of the plant.

4 Claims, No Drawings

THREE-STEP BIOMETHANATION PROCESS

The present invention claims priority from the Indian application number 1063/MUM/2005 dated May 9, 2005.

TECHNICAL FIELD

The present invention relates to a triphasic biomethanation process. More particularly, it relates to a triphasic biomethanation process wherein a commercially available biomass that is rich in starch or sugar is converted into a combustible mixture of methane and carbon dioxide using microbial consortia.

BACKGROUND AND PRIOR ART

In the conventional method, the gasification of biomass is done by heating the biomass with a controlled air supply to produce a mixture of hydrogen and carbon monoxide. This mixture is combustible and can be burnt as a source of energy.

Alternatively, many waste materials such as cow dung, sewage, spent wash or other effluents, are microbially converted into a combustible mixture of methane and carbon dioxide that can be used as an energy source. This conversion involves the stages of hydrolysis of biomass, its conversion into short chain fatty acids and their further conversion into a mixture of methane and carbon dioxide. The three stages of conversion, each brought about microbiologically, are invariably brought about using a single reactor, although in rare cases, the third stage is separated from the first two. The waste materials are utilized as and when available and the conversion is primarily aimed at reducing the polluting load in an economical manner. In case of cow dung the presently operated single stage system is ideally designed for domestic use in rural areas.

DEFICIENCIES OF PRIOR ART

1. That the thermal gasification of biomass is essentially used for ligninous materials. It uses a substantial part of the feed for generating heat that brings about the conversion of carbonaceous matter into a mixture of hydrogen and carbon monoxide. The conversion efficiency is low.
2. That the generation of biogas from industrial waste/cow dung suffers from the following drawbacks:

Presently available plants/processes combine the three stages of microbial conversion in one (in rare cases two) reactor. The conditions prevailing in the reactor are thus sub-optimal for each set of microorganisms. This results in slowing down of the conversion process.

In conditions of overloading of feeds, whereas the conversion to short chain fatty acids keeps pace with the feed input, the conversion to methane does not. This increases the acidity of the system, destroys methane generating microorganisms and leads to a further accumulation of acids. The system goes in a tailspin and the reactor stops functioning.

Whereas the cow dung based biogas plants keep getting a fresh supply of microorganisms (from fresh dung) continuously, such is not the case with waste based or other feed based biogas plants. Hence when these plants turn acid and stop functioning, the microbial consortia need to be built up all over again causing long shut down periods.

The relatively low concentration of the organic matter in the feed drain out larger volumes at high loading factors. This results in increased reactor volumes and high capital costs.

Use with starch-rich substrates frequently results in ethanol as an end product under anaerobic conditions.

The present invention provides a triphasic biomethanation process, which uses commercially available biomass rich in starch or sugar. In this triphasic process the process parameters at each phase of the process are controlled resulting in reduction in the retention time and an increase in the yield of the mixture of methane and other gases produced, with methane in high concentration.

The mixture of methane and carbon dioxide may be used for cooking purposes or for generating electricity. This mixture can also be converted to purified methane and compressed as CNG for use in vehicles.

Further the present invention facilitates generation of a source of energy on tap, from commercially available, renewable commodities in a cost effective manner.

Further the process of the present invention makes it possible to generate biogas for kitchen fuels, electrical power or transportation from renewable biomass in a cost effective manner especially in view of the threat that in the immediate future stocks of fossil fuel will run out. In addition, zero carbon emission based processes offer great potential.

OBJECT OF THE INVENTION

The object of the present invention is to develop a triphasic biomethanation process wherein energy in the form of biogas is obtainable from readily available agricultural commodities at competitive generation cost.

Another object of the present invention is to provide a process for conversion of starch or sugar into a combustible mixture of methane in an efficient, reliable and reproducible manner for producing clean gaseous fuel at a competitive cost.

The foregoing object of the invention is accomplished and the problems and shortcomings associated with prior art techniques and approaches are overcome by the present invention described in the present embodiment.

STATEMENT OF INVENTION

The present invention relates to a triphasic biomethanation process which comprises the steps of:

adding agricultural feed into first reactor tank;
solubilizing the feed by heating to a temperature of 40+ C. to 90° C.;
subjecting the feed to moist heat;
hydrolyzing the feed by adding at least one enzyme or microbial population capable of producing required enzymes and allowing to react for 1 to 24 hours;
adding hydrolysate from the first reactor tank into second reactor for conversion into short chain fatty acids;
adding enriched microbial consortia to the hydrolysate in the second reactor;
heating the hydrolysate to a temperature between 30° C. to 50° C. with occasional stirring for 30 hours to 72 hours;
adding acid rich mixture obtained from second reactor in third reactor;
adding methanogenic microorganisms to the acid rich mixture in third reactor; and
heating the mixture to a temperature between 30° C. to 50° C. for 70 to 96 hours under anaerobic conditions to obtain a methane rich gas mixture being not less than 500 liters per kilogram of starch or sugary substance in the feed and the methane content of the gas so evolved is not less than 55%.

DETAILED DESCRIPTION

Detailed descriptions of the preferred embodiments are provided herein; however, it is to be understood that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or matter.

The process according to the present invention is segregated into three distinct stages and conditions of air access, pH retention time; microbial consortia etc. are optimized separately for each stage. The Microbial consortia for each stage are separately grown to target a given feed and are made readily available, to cut down gestation periods at start-up or while commissioning. Further, the hydrolytic reaction, which is the first stage of the process, is speeded up by providing appropriate physical/enzymatic/microbial environment. Further, the microbial consortia are so adjusted as to block the formation of ethanol. The acid generation stage is segregated from the methane generation stage. This enables a controlled entry of acid in the third stage. The methane generating microorganisms are active in this stage and these are susceptible to high acidity conditions. Feed concentration to the system is slightly raised. This reduces the volume of feed entering and leaving the system and concomitant loss of methane generating microorganisms with the effluent. The dependence on ready availability of feed is overcome by switching over to commercially available commodities.

According to the present invention, a triphasic biomethanation process for converting starch or sugary agricultural feed stock into a methane rich gas mixture comprises adding agricultural feed into the first reactor tank and subjecting it to moist heat. The temperature in the first reactor tank is maintained at 40 to 90° C. Further, at least one enzyme or microorganism capable of producing the required enzyme, is added to the above-mentioned dissolved agricultural feed. The mixture of the feed and enzymes is allowed to react for a period of 1 to 24 hours in the first reactor.

The agricultural feed is preferably rich in starch or sugar. It is selected from the ones that are most suitable for a given plant location such as crude tapioca starch, maize powder, sorghum, sugarcane, rain damaged grains when available, high sugar containing palm saps, cakes left after extraction of non-edible oil seeds, starchy tubers of all kinds, etc. A preliminary analysis of the agricultural feed helps in deciding the input level of the feed in the system and parameters for the first stage of attack.

The enzyme added maybe amylase, proteases, etc. The microorganisms added maybe *Bacillus subtilis, Clostridium propionicum*, etc.

Further, the hydrolysate obtained at the end of reaction from first reactor is added to the second reactor where it is converted into short chain fatty acids.

The hydrolysate is subjected to an enriched microbial consortium, specifically prepared for the hydrolysate of the particular feed. This consortium is specifically prepared for the particular feed as target and is enriched from natural microbial mixtures such as cow dung, sewage, etc. by a process of restricting its nutrition to the subject feed over a period of time. Once enriched the consortium is propagated and made available for deployment in the reactor. The reaction in the second reactor is carried out at a temperature between 30° C. to 50° C. for 24 to 72 hours along with occasional stirring.

The microorganisms for preparation of the enriched consortium may be selected from propagated from cowdungm sewage or effluent ponds near industries using the identified feeds.

The acid rich mixture from the second reactor is introduced into the third reactor. The mixture maybe neutralized with lime during the first few days, if required. It is subjected to methanogenic microorganisms. The temperature is maintained between 30° C. to 50° C. for 70 to 96 hours and the mixture is stirred occasionally. The reactor is protected from exposure to oxygen in the air and monitored for acid accumulation.

The methane rich gas starts evolving by 24 hours. The gas so generated is not less than 500 lit/kg of starchy/sugary substance in the feed and has methane content of not less than 55%. It can be stirred suitably and used directly for burning or stripped of contaminating gases and used either as feed stock in internal combustion engines for power generation or compressed (CNG) and made available for use in vehicles.

The segregation of the overall process into three distinct stages has made it possible to optimize the conversion efficiency of each stage and readjust its input/output levels as also the microbial population that brings about the conversion. Separation of the group of microbial consortium that converts the short chain fatty acids to methane from the other two stages has made it possible to protect this very susceptible group from high acidity levels and exposure to aerobic conditions. That by suitably adjusting the concentration of the organic matter that is allowed to flow through the system, it has become possible to reduce the volume of the effluent and thereby the loss of methanogenic microorganisms from the third stage. This has, in turn, conserved the population of this group, which are the slowest growers of all. Building up an independent stock of these three groups of microbial consortia in a separate facility has made it possible to commission or restart a plant with a relatively short gestation period.

The process is versatile and can be carried out using any starch-rich or sugar-rich feed stock that is advantageous in a location The present invention is further illustrated by the following non-limiting examples:

Example 1

One kilogram of karanja de-oiled cake was suspended in ten litre of water and subjected to the action of amylase at 70° C. After holding the feed at this temperature for one hour, it was cooled to 37° C., subjected to the action of protease and passed on to stage two of the system. The reactor used for this stage contained a suitable enriched consortium of micro organisms capable of converting the hydrolysed organic matter into short chain fatty acids. The reactor was maintained at 37+/−2 degrees centigrade and stirred occasionally. This was followed by a similar addition on the following day. On the third day, ten litre of acid mixture was passed on to the third stage that was carried out in a similar reactor, held at 37+/−2 degrees centigrade and similarly stirred, that contained an enriched microbial consortium of methanogenic bacteria. This addition was repeated into the reactor on five successive days to fill up this reactor to 50% of its capacity. Form the sixth day, ten litre of the reaction mixture from the third stage was discarded every day and was replenished with ten litre of acid mixture. The gas got generated daily, as a result of conversion in this stage, and was collected in a conventional manner and measured 550 litres comprising of 60% of methane. The whole process is repeated in a continuous fashion so that the system received one kilogram of cake every day and gave out not less than 500 litre of gas every day.

Example 2

One kilogram of tapioca starch was used as feed and the process was carried out in the same manner as in example 1. The feed was subjected to amylase in this case. The daily generation of gas in this system was not less than 620 litres comprising of 62% of methane.

Example 3

One kilogram of maize powder was used as feed and the process was carried out in the same manner as in example 1. The enzyme added was amylase followed by protease. The small amount of un-reacted solid residue at the end of Stage1 was removed and discarded. The daily generation of gas was not less than 580 litres comprising of not less that 60% of methane.

ADVANTAGES OF THE INVENTION

1. It uses renewable starch-rich/sugary agro-products as feedstock to generate a combustible gas, in a cost effective manner.
2. It cuts down start up or re-commissioning period for a plant.
3. It uses three segregated stages to bring about the conversion whereby reactions in each stage are carried in a highly efficient manner and under optimal conditions thereby substantially increasing efficiency and reducing plant size.
4. It prevents the formation of alcohol.

The invention claimed is:

1. A triphasic biomethanation process for converting starch or sugary agricultural feed stock into a methane rich gas mixture comprising of dissolution and hydrolysis of agricultural feed rich in starch and sugar at temperatures between 40° C. to 90° C., subject to the moist heat; thereafter the agricultural feed is exposed to appropriate enzymes or to microbial populations or a combination of enzymes and is carried out in less than 24 hours; the product obtained from the hydrolysis process is led in second reactor to convert the hydrolysed submits into short chain fatty acids, subject to enriched microbial consortia that is enriched from natural biological mixtures; this acidogenesis reaction is carried out between temperatures 30° C. to 50° C. with occasional stirring of the mixture; the reactor size is optimized according to microbial population and the retention time required for conversion is usually less than 72 hours; the output is subjected to methanogenesis by methanogenic micro-organisms for converting the short chain fatty acids into a mixture of methane, carbon dioxide and traces of hydrogen sulphide; depending upon the feed material and the methane rich gas, being not less than 500 litres per kilogram of starch/sugary substance of the feed and the methane content of the gas so evolved is not less than 55%, starts evolving; the effective retention time in this stage being less than 96 hours and thereby the process gets completed in three stages, enabling the operation of each stage at its optimal condition.

2. A triphasic biomethanation process for converting starch or sugary agricultural feed stock into a methane rich gas mixture as claimed in claim 1 wherein crude tapioca starch which is rich in starch, is converted into a methane gas mixture.

3. A triphasic biomethanation process for converting starch or sugary agricultural feed stock into a methane rich gas mixture as claimed in claim 1 wherein maize powder which is rich in starch, is converted into a methane gas mixture.

4. A triphasic biomethanation process for converting starch or sugary agricultural feed stock into a methane rich gas mixture as claimed in claim 1 wherein sugarcane which is rich in sugar, is converted into a methane gas mixture.

* * * * *